United States Patent [19]

Rosso et al.

[11] 4,323,557
[45] Apr. 6, 1982

[54] PRESSURE-SENSITIVE ADHESIVE CONTAINING IODINE

[75] Inventors: Paul D. Rosso, St. Joseph Township, St. Croix County, Wis.; Michael Y. Moss, St. Paul, Minn.

[73] Assignee: Minnesota Mining & Manufacturing Company, St. Paul, Minn.

[21] Appl. No.: 62,362

[22] Filed: Jul. 31, 1979

[51] Int. Cl.³ .................. A61K 9/70; A61F 13/00; A61L 15/03; A61K 31/79
[52] U.S. Cl. .................................... 424/28; 424/80; 424/150; 128/155; 128/156; 128/268
[58] Field of Search .............. 424/28, 80, 81, 150; 128/155, 156, 268

[56] References Cited

U.S. PATENT DOCUMENTS

| | | |
|---|---|---|
| 2,400,389 | 5/1946 | Cavalito . |
| 2,427,022 | 9/1947 | Russ et al. . |
| 2,739,922 | 3/1956 | Shelanski ........................... 424/150 |
| 2,752,281 | 6/1956 | Niederhauser . |
| 2,826,528 | 3/1958 | Shelanski . |
| 2,853,417 | 9/1956 | Werner . |
| 2,927,914 | 3/1960 | Lee . |
| 2,951,766 | 9/1960 | White . |
| 3,028,300 | 4/1962 | Cantor et al. ........................ 424/150 |
| 3,028,300 | 4/1962 | Cantog et al. . |
| 3,307,544 | 3/1967 | Gander et al. . |
| 3,347,233 | 10/1967 | Migilarese . |
| 3,577,516 | 5/1971 | Gould et al. . |
| 3,579,628 | 5/1971 | Gander et al. . |
| 3,598,123 | 8/1971 | Zaffaroni ........................... 128/268 |
| 3,632,740 | 1/1972 | Robinson .............................. 424/28 |
| 3,645,835 | 7/1969 | Smith . |
| 3,645,835 | 2/1972 | Hodgson . |
| 3,728,148 | 4/1973 | Pietsch et al. . |
| 3,734,097 | 5/1973 | Zaffaroni ........................... 128/268 |
| 3,749,772 | 7/1973 | Cardarelli ........................... 424/150 |
| 3,769,071 | 10/1973 | Trancik ........................... 117/122 P |
| 3,886,268 | 5/1975 | Halpern .............................. 424/80 |
| 3,896,789 | 7/1975 | Trancik . |
| 3,898,326 | 8/1975 | Cantor et al. ........................ 424/80 |
| 3,907,720 | 9/1975 | Field et al. . |
| 3,969,498 | 7/1976 | Catania et al. . |
| 3,996,934 | 12/1976 | Zaffaroni . |
| 4,045,364 | 8/1977 | Richter . |
| 4,073,291 | 2/1978 | Marvel et al. . |
| 4,094,967 | 6/1978 | Gilbert ................................. 424/28 |
| 4,113,851 | 9/1978 | Leveen et al. ...................... 424/150 |
| 4,113,857 | 9/1978 | Shetty ................................. 424/150 |
| 4,147,775 | 4/1979 | Schwartz et al. ................... 424/150 |
| 4,151,275 | 4/1979 | Cantor et al. ...................... 424/150 |

FOREIGN PATENT DOCUMENTS

| | | |
|---|---|---|
| 11471 | 12/1979 | European Pat. Off. . |
| 685805 | 12/1939 | Fed. Rep. of Germany . |
| 1925348 | 5/1969 | Fed. Rep. of Germany . |
| 2012548 | 6/1970 | France . |
| 1213295 | 11/1970 | United Kingdom . |
| 1471402 | 1/1974 | United Kingdom . |
| 1533406 | 2/1975 | United Kingdom . |
| 578971 | 7/1978 | U.S.S.R. . |

OTHER PUBLICATIONS

Chem. Abstracts 66 #88643h (1967) of Neth. Appl. 6,507,109.
Chem. Abstracts 77 #92889 (1972) of Ger. 1,593,155.
Chem. Abstracts 78 #106374a (1973) Aussems et al.
Chem. Abstracts 89 #36658x Knuutils et al.
Chem. Abstracts 79 #70235k (1973) of Ger. Off. 2,263,130.
Chem. Abstracts 82 #77112p (1975) of Ger. Off. 2,417,872.
Chem. Abstracts 85 #14541u, #57405v #72841d (1976) Hegnae.

*Primary Examiner*—Shep K. Rose
*Attorney, Agent, or Firm*—Cruzan Alexander; Donald M. Sell; Gary L. Griswold

[57] ABSTRACT

A process for making a stable chemical complex of iodine, an iodide ion and a dermatologically acceptable room temperature tacky pressure-sensitive adhesive which is substantially free of acidic components. The resulting composition exhibits broad-spectrum antimicrobial activity when placed in contact with mammalian skin.

8 Claims, No Drawings

PRESSURE-SENSITIVE ADHESIVE CONTAINING IODINE

This invention relates to a process for making dermatologically acceptable pressure-sensitive adhesive containing iodine. An aspect of this invention relates to the ability of the resulting composition to exhibit antiseptic broad-spectrum antimicrobial activity in a controlled and sustained manner.

Numerous pathogens are present on the human skin. In a hospital environment it is generally desired that the growth of disease-producing microorganisms be inhibited and preferably that these microorganisms be destroyed so as to control patient infection and encourage wound healing. As a result, the application to the skin surface of topical bactericidally active agents has become a standard part of the aseptic hospital technique.

One often used antimicrobial agent is iodine but because of its inherent chemical and physical limitations, its use as an antiseptic broad-spectrum antimicrobial has been limited. Elemental iodine has a high vapor pressure which causes great loss in germicidal potency as the iodine content volatilizes from antiseptic preparations containing iodine as the antimicrobial agent. Moreover, iodine is generally not occluded with bandages because of potential for corrosive destruction of skin.

In order to preserve the antimicrobial activity of iodine and at the same time reduce the corrosive properties and vapor pressure, complexes of polyvinylpyrrolidone and iodine have been formed. An example of the synthesis of one such polyvinylpyrrolidone-iodine complex (PVP-I) is disclosed in U.S. Pat. No. 4,128,633.

The topical applications of broad-spectrum antimicrobials have been in the form of preoperative skin preps, surgical scrub tissues, e.g. U.S. Pat. No. 4,045,364, washes, wound cleaners, lotions and ointments. In some instances such a delivery is effective for the particular purpose for a limited period of time. Microorganisms that may have survived the initial application of the antimicrobial agent act as a seed to cause the pathogen population in some instances to rise to their initial levels. Continuous application of an antimicrobial agent to the site is a means of inhibiting the increase in population.

While numerous other biologically active agents have been incorporated into adhesive layers on a substrate to provide a continuous application to the body of the agent, there has been no successful incorporation of a broad-spectrum antimicrobial into an adhesive layer which has been characterized by stability and unaltered activity of the broad-spectrum antimicrobial. Examples of various other agents that have been incorporated into adhesives are U.S. Pat. No. 2,137,169 where phenol, thymol, menthol, etc. are added to a starch adhesive; U.S. Pat. No. 3,249,109 where benzocaine was added to a tacky gelatin; U.S. Pat. No. 3,632,740 where a corticosteroid is added to an adhesive; U.S. Pat. No. 3,734,097 where a microencapsulated anti-neoplastic agent is added to an adhesive; U.S. Pat. No. 4,073,291 where Tretinoin is added to an adhesive; U.S. Pat. No. 3,769,071 where 5-fluorouracil is incorporated into an adhesive; and U.S. Pat. No. 3,896,789 where retinoic acid is incorporated into a pressure sensitive tape. Previous attempts at incorporating broad-spectrum antimicrobials into adhesives have been frustrated by reduced biological activity, and uncontrollable release which causes skin irritation in some patients.

The term broad-spectrum is used herein to mean that the antimicrobial exhibits activity against more than one type of microorganism, i.e. both gram positive and gram negative bacteria and would very likely also have activity against fungi and viruses (Reference: Federal Register, Vol. 39, No. 179).

The present invention may be generally described as a process for the formation of a chemical and storage stable composition which when placed in contact with the skin uniformly and controllably releases the broad-spectrum antimicrobial agent iodine. This release occurs with substantially unaltered broad-spectrum antimicrobial activity even after being subjected to irradiation sterilization. This antiseptic antimicrobial activity is accomplished by the present invention with essentially no skin irritation.

The resulting composition of the process of the present invention is a stable chemical complex of iodine, an iodide ion and a dermatologically acceptable normally room temperature tacky pressure sensitive adhesive (PSA). By "stable" it is meant that a composition coating of 11 grains per 24 sq. in. which is attached to a polyethylene sheet can be exposed to a temperature of 120° F. and a relative humidity of 9% for two (2) weeks or to a dose of 2.5 megarads of gamma irradiation without substantial alteration of the physical appearance or of the chemical activity, as tested by the starch test and microbiological activity as tested by Zone Inhibition Assay.

The Zone Inhibition Assay test is performed as follows: An assay bacterium *Bacillus subtilis* is grown in rotary shake culture (200 rpm) for approximately 6 hours at 37° C. The growth medium, L-broth, consist of the following ingredients dissolved in 1 L of distilled water and adjusted to pH 7.0: tryptone 10 g, yeast extract 5 g, sodium chloride 10 g, glucose 1 g. This culture is diluted in sterile L-broth to 50% T at 660 mu, further diluted 1:10, and inoculated at a ratio of 1:100 into molten soybean-casein digest agar medium (Inolex) maintained at 45°–50° C. Assay plates are prepared by first pipesetting a 5 ml base layer of soybean-casein digest agar medium (TSA), allowing this to harden at room temperature in disposable petri dishes, and then overlaying with 5 ml of seeded TSA. These preparations are used the same day.

Coated polyethylene films (prepared in the manner taught in the Example below) are tested in the same way regardless of the antimicrobial incorporated into the adhesive layer. Ten 6 mm discs are cut from an evenly coated area (i.e. no visible flaws) with a heavy duty paper punch (Master Products, Series 25). The paper backing is removed from the coated disc with the aid of forceps and microspatula. The coated disc is then placed adhesive-side down on the seeded-agar surface, 4 per plate.

Iodine reference discs are then prepared. A solution containing 10 percent iodine is prepared by dissolving 1 g of iodine and 1 g of sodium iodide in 10 percent aqueous acetone using a 10 ml volumetric flask. This stock solution, freshly prepared and the same solvent is used to prepare 0.25, 0.5, 0.75 and 1.0 percent iodine solutions. From these dilutions, 10 ul aliquots are applied to 6 mm polyester fabric discs placed on the seeded agar surface to provide discs containing 25, 50, 75 and 100 ug iodine each. (The polyester fabric should be leached overnight in solvent to remove inherent antibacterial activity prior to punching.) Each reference disc is covered with a 1 inch square of 2-ml polyethylene to prevent vaporization prior to diffusion through the underlying agar.

The coated discs and reference disc assay plates are incubated overnight at room temperature. Zones of inhibition around the discs were measured to the nearest 0.5 mm with the aid of a binocular stereoscopic microscope. In the case of iodine antimicrobials, the coated discs are also removed to examine plates for areas of growth inhibition under the discs.

Assay results for reference antimicrobials using the preceding methods demonstrate that the diameter of the zone of inhibition measured in mm is linearly proportional to $LOG_{10}$ concentration for each agent over the range examined. The release of antimicrobial from the adhesive of the present invention can be estimated by graphic interpolation of the inhibition values.

The starch test is performed as follows: An indicator solution is prepared by dissolving 62.5 g of paragon Iodine Titration Indicator (Eastern Chemical, Division of Guardian Chemical Corp., Hauppauge, N.Y.) in 250 ml. of distilled water with stirring. A drop of the Paragon Indicator solution from then is placed on the adhesive surface. Formation of blue coloration in the drop indicates availability of iodine.

The process for forming the composition of the present invention involves forming a pressure sensitive adhesive and mixing into it an antimicrobial treating solution comprising iodine, an iodide, and a solvent. The resulting composition preferably contains N-vinyl-pyrrolidone (NVP) in the backbone of the pressure-sensitive adhesive which serves to complex iodine. It is believed that complexation provides stability while maintaining an appropriate equilibrium to provide sustained release of iodine.

The composition which is the resulting chemical complex of the aforementioned process is stable, nonirritating, non-sensitizing, non-toxic and non-traumatizing to skin or other tissues. Although it is generally recognized that an acid medium renders many broad-spectrum antimicrobial agents more stable, i.e. PVP-I, it has been found that a pressure sensitive adhesive having a significant acidic content causes a negative alteration in the stability of iodine in the present system. Therefore it is desirable that the normally room temperature tacky pressure-sensitive adhesive monomers which is to act as the base of the present composition be substantially free of acidic components. By "substantially free of acidic components" it is meant that the pressure-sensitive adhesive monomers be substantially free of substituent groups which exhibit acid functionality, e.g., acrylic acid, etc. Examples of adhesive monomers which can be utilized in the preparation present antimicrobial composition PSA include acrylics and vinyl/acrylics. The formulation of these adhesives are well known in the art, e.g. U.S. Pat. Nos. R. 24906, 2,973,286; 3,307,544, 3,728,148, etc. It will be appreciated by one skilled in the art that the aforestated adhesive types might also include various chemical modifiers so as to enable them to have the utility dictated by the situation, e.g. tackifiers, crosslinkers, stabilizers, initiators etc. The preferred pressure sensitive adhesive for use in this invention is a copolymer comprised of N-vinylpyrrolidone (NVP) and isooctyl acrylate (IOA).

It is believed that the iodine release is controlled by the copolymerization of low levels of the NVP into the adhesive backbone. The iodine release from the adhesive matrix is a function of the level of NVP copolymerized into the adhesive backbone. For a given iodine content, the higher the NVP level, the lower the antimicrobial activity. For this invention, the useful NVP comonomer level is less than 30% (preferentially 5-10%) of the total adhesive solids. At higher NVP levels, skin adhesion and antimicrobial activity are reduced.

An antimicrobial solution is used to incorporate iodine into the pressure sensitive adhesive. This solution contains iodine, inorganic iodide (e.g., potassium iodide) and a suitable solvent compatible with the adhesive. A solution recommended for use with the 5-10% NVP copolymer adhesive above would have a 0.5:1 to 4:1 molar ratio of iodide:iodine dissolved in denatured ethanol (preferred solution, 2:1 molar ratio of iodide:iodine). For example, a solution utilizing sodium iodide would have a formulation of 1-20 wt.% iodine, 1.2-24 wt.% sodium iodide and 97.8-56 wt.% ethanol.

Although the mechanism of complexation of iodine into the adhesive matrix of this invention is not completely understood, it is believed to have some analogy to the complexation of iodine with polyvinylpyrrolidone. The following is one possible representation of the complex of the present invention:

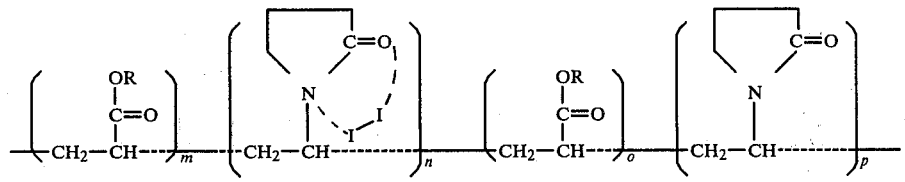

where m, n, o and p are integers.

The composition of the process of the present invention may be either attached directly onto a flexible backing substrate or formed onto a release liner for later use. The backing may be any material known for use in medical application with the preferred material being polyethylene film. The solvents are then evaporated by means known to the art whereby an adhesive film is formed which is useable in or on tapes, drapes and other medical devices.

The invention is further illustrated by the following non-limiting example:

A solution polymer adhesive of composition isooctyl acrylate/N-vinylpyrrolidone/γ-methacryloxypropyl trimethoxysilane (94.95/5/0.05) is prepared by polymerization in ethyl acetate/heptane/ethanol (48/47/5) (Conditions: nitrogen atmosphere, azobisisobutyronitrile initiator, 6 hours at 53° C.; Properties: total solids=45%, intrinsic viscosity=0.8).

The following formulation is prepared:

adhesive from above 500 g.
a solution containing 20 wt. % iodine/24 wt. %

| -continued | |
|---|---|
| sodium iodide in denatured ethanol | 11 g. |
| additional denatured ethanol | 78 g. |
| a 10 wt. % solution of p-toluenesulfonic acid (p-TSA) in denatured ethanol (0.1 wt. % p-TSA on adhesive solids) | 2.3 g. |

The formulation is stirred at room temperature with a spatula to yield a uniform solution of 1 wt.% iodine/1.2 wt.% sodium iodide on adhesive solids. This solution is coated onto a silicone release liner and dried (10 min., 175° F.) to form a homogeneous, iodine-colored adhesive film of coating weight equal to 11 grains/24 sq. in. The adhesive film is laminated to a backing of a corona and quatarnary amine antistat treated polyethylene to form a construction containing the antimicrobial iodine. This construction exhibited an activity when applied in vivo on seeded human skin of a four (4) log reduction of Staphylococcus aureus and Pseudomonas aeruginosa after one hour. The construction exhibited satisfactory adhesion and stability after sterilization by irradiation.

What is claimed is:

1. In a process for making a composition which exhibits antiseptic broad-spectrum antimicrobial activity when placed in contact with the skin, the improvement comprising forming a solution of an iodide, a solvent and iodine, and reacting said solution with a dermatologically acceptable pressure-sensitive adhesive.

2. In a composition which exhibits antiseptic broad-spectrum antimicrobial activity when placed in contact with the skin, the improvement comprising a stable chemical complex of an iodide, iodine and a dermatologically acceptable pressure-sensitive adhesive.

3. The composition of claim 2 wherein said dermatologically acceptable pressure-sensitive adhesive is substantially free of acidic components.

4. In a flexible sheet material having attached thereto a dermatologically acceptable pressure-sensitive adhesive, the improvement comprising said dermatologically acceptable, pressure-sensitive adhesive being a stable chemical complex of an iodide, iodine and a dermatologically acceptable pressure-sensitive adhesive.

5. The composition of claims 2 and 4 wherein said pressure-sensitive adhesive is a copolymer comprising isooctyl acrylate and N-vinyl-pyrrolidone.

6. The sheet material and adhesive of claim 4 in the form of a medical device.

7. The sheet material and adhesive of claim 4 in the form of a tape.

8. The sheet material and adhesive of claim 4 in the form of a drape.

* * * * *